United States Patent
Sugiura

(10) Patent No.: US 7,514,093 B2
(45) Date of Patent: Apr. 7, 2009

(54) VITREOUS ANTIMICROBIAL AGENT AND ANTIMICROBIAL PRODUCT

(75) Inventor: Koji Sugiura, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 524 days.

(21) Appl. No.: 10/543,100

(22) PCT Filed: Jan. 26, 2004

(86) PCT No.: PCT/JP2004/000661

§ 371 (c)(1),
(2), (4) Date: Jul. 22, 2005

(87) PCT Pub. No.: WO2004/064524

PCT Pub. Date: Aug. 5, 2004

(65) Prior Publication Data

US 2006/0127498 A1    Jun. 15, 2006

(30) Foreign Application Priority Data

Jan. 24, 2003    (JP) .............................. 2003-016274

(51) Int. Cl.
*A01N 25/00* (2006.01)
*A01N 59/00* (2006.01)
*A01N 59/06* (2006.01)
*A01N 59/14* (2006.01)
*A01N 59/16* (2006.01)
*C03C 3/04* (2006.01)
*C03C 3/064* (2006.01)
*C03C 3/066* (2006.01)
*C03C 3/068* (2006.01)
*C04B 35/00* (2006.01)
*C04B 35/50* (2006.01)

(52) U.S. Cl. .................. 424/405; 424/618; 424/641; 424/657; 424/692; 424/722; 424/724; 424/489; 501/53; 501/77; 501/78; 501/79; 501/152; 501/154

(58) Field of Classification Search ................ 501/79
See application file for complete search history.

(56) References Cited

U.S. PATENT DOCUMENTS

| | | | |
|---|---|---|---|
| 4,931,078 A | 6/1990 | Yamamoto | |
| 5,049,139 A | 9/1991 | Gilchrist | |
| 5,296,238 A | 3/1994 | Sugiura et al. | |
| 5,766,611 A | 6/1998 | Shimono et al. | |
| 6,831,028 B1 | 12/2004 | Ishii et al. | |

FOREIGN PATENT DOCUMENTS

| | | | | |
|---|---|---|---|---|
| JP | 3-124810 | A | | 5/1991 |
| JP | 7-291654 | A | | 11/1995 |
| JP | 07-291654 | A | * | 11/1995 |
| JP | 8-48539 | A | | 2/1996 |
| JP | 11-228171 | A | | 8/1999 |
| JP | 2000-191339 | A | | 7/2000 |
| JP | 2000-203876 | A | | 7/2000 |
| JP | 2000-281380 | A | | 10/2000 |
| JP | 2000-302478 | A | | 10/2000 |
| JP | 2001-26438 | A | | 1/2001 |
| JP | 2001-247726 | A | | 9/2001 |
| JP | 2002-3239 | A | | 1/2002 |
| JP | 2002-003239 | A | * | 1/2002 |
| JP | 2002-37643 | A | | 2/2002 |
| JP | 2002-037643 | A | * | 2/2002 |

* cited by examiner

*Primary Examiner*—John Pak
*Assistant Examiner*—Nathan W Schlientz
(74) *Attorney, Agent, or Firm*—Sughrue Mion, PLLC

(57) ABSTRACT

A vitreous antimicrobial agent that can exhibit excellent antimicrobial properties when added to various types of resins, that has excellent discoloration resistance and hot water resistance, and that can easily be produced at a commercial scale. The vitreous antimicrobial agent includes, relative to 100 mass % of total glass components, 0.1 to 2 mass % of $Ag_2O$, 40.5 to 49 mass % of ZnO, 6 to 9.5 mass % of $SiO_2$, 30.5 to 39.5 mass % of $B_2O_3$, 2 to 10 mass % of an alkaline earth metal oxide, and 6 to 7.5 mass % of $Na_2O$; the vitreous antimicrobial agent comprising, in addition to these, 0.01 to 5 mass % of $CeO_2$ as necessary. An antimicrobial resin composition and an antimicrobial product including the vitreous antimicrobial agent.

12 Claims, No Drawings

VITREOUS ANTIMICROBIAL AGENT AND ANTIMICROBIAL PRODUCT

The present application is a national stage entry of PCT/JP04/00661 filed 26 Jan. 2004.

TECHNICAL FIELD

The present invention relates to a silver- and zinc-containing vitreous antimicrobial agent and to an antimicrobial resin composition and an antimicrobial product comprising the antimicrobial agent.

BACKGROUND ART

As conventional inorganic antimicrobial agents, those in which an antimicrobial metal such as silver or copper is supported on apatite, zeolite, glass, zirconium phosphate, silica gel, etc. are known. Compared with organic antimicrobial agents, they have high safety, and do not evaporate or decompose, thus having a long-lasting antimicrobial effect and, moreover, they have excellent heat resistance. Because of this, antimicrobial resin compositions obtained by mixing these antimicrobial agents with various types of polymer compounds are molded into antimicrobial products in the form of various types of moldings, fibers, and films and are used in various types of applications.

Among these, vitreous antimicrobial agents comprising an antimicrobial metal such as silver, copper, or zinc have the characteristics that the glass grain size, the refractive index, and leaching properties of antimicrobial metal can easily be controlled according to the intended application, and they are therefore added to antimicrobial resin compositions for various types of applications.

For example, a silver-containing vitreous antimicrobial agent has been proposed (ref., e.g. JP-A-03-124810). Furthermore, a vitreous antimicrobial agent comprising a high concentration of zinc has been proposed (ref., e.g. JP-A-2001-26438).

Although the conventional silver-containing vitreous antimicrobial agent (also called a silver-based vitreous antimicrobial agent) has the advantage that a high antimicrobial effect can be obtained with a relatively low concentration of silver, there are the problems that, due to heat when kneading with a resin or due to exposure to UV rays after processing of the resin, degradation and deterioration of the resin itself are accelerated or the resin product is discolored, and the excellent characteristics of the resin product itself are thus often impaired. Furthermore, when the vitreous antimicrobial agent comprising silver alone as the antimicrobial component is kneaded with certain resins, such as an ABS resin or an acrylic resin, it is difficult for the antimicrobial effect to be exhibited.

On the other hand, when the vitreous antimicrobial agent comprising a high concentration of zinc alone is kneaded with a resin, it causes little degradation, deterioration, or discoloration of the resin, but compared with the silver-containing glass, the antimicrobial properties can be poor in some cases, and if an attempt is made to make the resin composition exhibit an adequate antimicrobial effect, it is necessary to increase the amount added to the resin, and as a result there is the problem that the physical properties of the resin itself are degraded.

In order to solve these problems, a vitreous antimicrobial agent comprising both silver and zinc has been proposed.

As an example of a composition comprising phosphoric acid, a vitreous antimicrobial agent comprising 0.2 to 5 wt % of $Ag_2O$, 1 to 50 wt % of ZnO, 30 to 80 wt % of $P_2O_5$, 1 to 20 wt % of CaO, and 0.1 to 5 wt % of $CeO_2$ has been proposed (ref. e.g. JP-A-2000-191339). A vitreous antimicrobial agent comprising 0.1 to 5 wt % of $Ag_2O$, 1 to 50 mol % of MgO+CaO+BaO+ZnO, 30 to 60 mol % of $P_2O_5$, 2 to 40 mol % of $B_2O_3$, at most 15 mol % of $Al_2O_3$, and at most 15 mol % of an alkali metal oxide has also been proposed (ref., e.g. JP-A-2001-247726). A vitreous antimicrobial agent comprising 0.03 to 5 mol % of $Ag_2O$, 0 to 30 mol % of ZnO+BaO, 0 to 20 mol % of $B_2O_3$, 0 to 2.5 wt % of $TiO_2$+CeO, 0 to 5 mol % of $SiO_2$, 20 to 55 mol % of MgO+CaO, 5 to 25 mol % of $Na_2O$, 40 to 55 mol % of $P_2O_5$, and 0 to 5 mol % of PbO has also been proposed (ref., e.g. JP-A-8-48539).

As an example of a composition comprising no phosphoric acid, a soluble vitreous antimicrobial agent comprising 20 to 50 wt % of $B_2O_3$, 50 to 80 wt % of ZnO, at most 10 wt % of an alkaline earth metal oxide, and at most 2 wt % of $Ag_2O$ has been proposed (ref., e.g. JP-A-2000-281380). A vitreous antimicrobial agent comprising 0.1 to 5 wt % of $Ag_2O$, 35 to 60 wt % of ZnO+MgO+CaO+BaO, 10 to 50 wt % of $SiO_2$, 0 to 20 wt % of $Al_2O_3$, 0 to 20 wt % of $Na_2O$+$K_2O$+$Li_2O$, 10 to 54 wt % of $B_2O_3$, 0 to 10 wt % of $TiO_2$, and 0 to 10 wt % of $La_2O_3$ has also been proposed (ref., e.g. JP-A-2000-302478). A vitreous antimicrobial agent comprising 0.05 to 5 wt % of $Ag_2O$, 0 to 30 wt % of ZnO, 0 to 20 wt % of MgO+CaO+BaO, 10 to 60 wt % of $SiO_2$, 0 to 20 wt % of $Al_2O_3$, 0 to 4.9 wt % of $Na_2O$+$K_2O$+$Li_2O$, and 10 to 60 wt % of $B_2O_3$ has also been proposed (ref., e.g. JP-A-2000-203876).

However, it is known that the vitreous antimicrobial agent comprising silver and, as a main component, $P_2O_5$, has poor hot water resistance. The glass comprising $B_2O_3$ as a main component has high hardness, it therefore abrades a metal surface of a mixer or a resin molder used for kneading it with a resin, and there is thus the problem that a metal powder formed by scraping contaminates the resin composition, thereby darkening the color of a final resin product. When a large amount of $B_2O_3$ is contained in the glass, as is the case for that comprising $P_2O_5$ as a main component, there might be problems caused by poor hot water resistance.

In order for a high antimicrobial effect, which can be provided for various types of processed resin products, to be exhibited, a glass composition having as high a concentration of zinc as possible and an appropriate amount of silver is effective. However, unless the concentrations of $P_2O_5$ and $B_2O_3$, which are glass framework-forming components, are reduced as much as possible, the relative ZnO concentration in the glass composition cannot be increased, and the problems with regard to hot water resistance, discoloration, and hardness when added to a processed resin product cannot be eliminated. Furthermore, a composition comprising a high concentration of zinc, as well as silver, which is easily reducible, can easily be prepared in a small amount such as at laboratory scale, but when commercial production of on the order of at least a few hundred kg is carried out, there is the problem that the glass is colored. It is therefore not easy to mass-produce an antimicrobial agent comprising a glass comprising silver, which has a high antimicrobial effect, and a high concentration of zinc.

DISCLOSURE OF INVENTION

It is an object of the present invention to provide a vitreous antimicrobial agent that can exhibit excellent antimicrobial properties when added to various types of resins, which has excellent discoloration resistance and hot water resistance, and which can easily be produced on a commercial scale. It is another object thereof to provide an antimicrobial resin composition and an antimicrobial product comprising the vitreous antimicrobial agent.

As a result of an intensive investigation by the present inventors in order to attain the above-mentioned objects, it has been found that a specified glass having a limited glass composition range can attain the above-mentioned objects, and the present invention has thus been accomplished. That is, the present invention relates to a vitreous antimicrobial agent comprising, relative to 100 mass % of total glass components, 0.1 to 2 mass % of $Ag_2O$, 40.5 to 49 mass % of ZnO, 6 to 9.5 mass % of $SiO_2$, 30.5 to 39.5 mass % of $B_2O_3$, 2 to 10 mass % of an alkaline earth metal oxide, and 6 to 7.5 mass % of $Na_2O$, to a vitreous antimicrobial agent comprising, in addition to these, 0.01 to 5 mass % of $CeO_2$ as necessary, to an antimicrobial resin composition that includes the vitreous antimicrobial agent, and to an antimicrobial product that includes the vitreous antimicrobial agent.

The present invention has been achieved based on the above-mentioned understanding, and representative examples thereof are cited below.

1. A vitreous antimicrobial agent comprising, relative to 100 mass % of total glass components, 0.1 to 2 mass % of $Ag_2O$, 40.5 to 49 mass % of ZnO, 6 to 9.5 mass % of $SiO_2$, 30.5 to 39.5 mass % of $B_2O_3$, 2 to 10 mass % of an alkaline earth metal oxide, and 6 to 7.5 mass % of $Na_2O$.
2. The vitreous antimicrobial agent according to 1 above, wherein the glass component further comprises 0.01 to 5 mass % of $CeO_2$.
3. The vitreous antimicrobial agent according to 1 above, wherein the vitreous antimicrobial agent is a powder and has an average particle size of 0.1 to 30 μm.
4. An antimicrobial resin composition comprising the vitreous antimicrobial agent according to any one of 1 to 3 above in an amount at which an antimicrobial function is exhibited.
5. An antimicrobial resin composition comprising the vitreous antimicrobial agent according to any one of 1 to 3 above at 0.03 to 5 parts by mass relative to 100 parts by mass of the antimicrobial resin composition.
6. An antimicrobial product comprising the vitreous antimicrobial agent according to any one of 1 to 3 above.

BEST MODE FOR CARRYING OUT THE INVENTION

The present invention is explained in detail below.

Vitreous Antimicrobial Agent

The antimicrobial agent of the present invention is a vitreous antimicrobial agent comprising at least Ag and Zn; a vitreous antimicrobial agent comprising, relative to 100 mass % of total glass components, 0.1 to 2 mass % of $Ag_2O$, 40.5 to 49 mass % of ZnO, 6 to 9.5 mass % of $SiO_2$, 30.5 to 39.5 mass % of $B_2O_3$, 2 to 10 mass % of an alkaline earth metal oxide, and 6 to 7.5 mass % of $Na_2O$; and a vitreous antimicrobial agent comprising in addition to the above 0.01 to 5 mass % of $CeO_2$ as necessary (hereinafter, when the percentage content of each of the component is mentioned, it is a percentage content relative to 100 mass % of the total glass components).

The glass components referred to in the present invention are $Ag_2O$, ZnO, $SiO_2$, $B_2O_3$, an alkaline earth metal oxide, and $Na_2O$, and include $CeO_2$ as necessary. The vitreous antimicrobial agent may include, in addition to these glass components, various types of oxidizing agents, additives, and other glass-forming components.

In the vitreous antimicrobial agent of the present invention, the percentage content of $Ag_2O$, which is a component imparting antimicrobial performance, is 0.1 to 2 mass %, preferably 0.4 to 1.5 mass %, and more preferably 0.6 to 1.4 mass %. It is difficult to convert $Ag_2O$ into a glass, and when it is added at more than 2 mass %, silver that has not been converted into a glass might be deposited as a metal. This also causes the problem that the metallic silver thus deposited might color the glass. On the other hand, when $Ag_2O$ is less than 0.1 mass %, the antimicrobial properties of the vitreous antimicrobial agent of the present invention might become insufficient.

The percentage content of ZnO, which together with $Ag_2O$ is a component that imparts antimicrobial performance to the vitreous antimicrobial agent of the present invention, is 40.5 to 49 mass %, preferably 42 to 48.5 mass %, and more preferably 43 to 48 mass %. If ZnO is added at more than 49 mass %, it is extremely difficult to form a glass, and there is the problem that when a molten glass is cooled during mass production the glass might be colored. On the other hand, if ZnO is less than 40.5 mass %, the antimicrobial properties of the glass of the present invention might become insufficient.

The $SiO_2$ component in the vitreous antimicrobial agent of the present invention is a component that forms a glass framework, and the percentage content of $SiO_2$ in the vitreous antimicrobial agent of the present invention is 6 to 9.5 mass %, preferably 6.5 to 9 mass %, and more preferably 7 to 8.5 mass %. If $SiO_2$ is added at more than 9.5 mass %, a processed resin product to which this vitreous antimicrobial agent is added might have difficulty in exhibiting antimicrobial properties and, in particular, antimicrobial properties after a hot water resistance test. On the other hand, if $SiO_2$ is less than 6 mass %, it might become difficult to form a glass.

The $B_2O_3$ component in the vitreous antimicrobial agent of the present invention is a component that forms a glass framework, and the percentage content of $B_2O_3$ in the vitreous antimicrobial agent of the present invention is 30.5 to 39.5 mass %, preferably 30.9 to 35.5 mass %, and more preferably 31.0 to 34.5 mass %. If $B_2O_3$ is added at more than 39.5 mass %, the color of a processed resin product to which this vitreous antimicrobial agent is added becomes blackish and tends to darken, and since the relative content of the antimicrobial component ZnO decreases it might become difficult for antimicrobial properties to be exhibited and, in particular, antimicrobial properties after a hot water or hydrothermal treatment. On the other hand, if $B_2O_3$ is less than 30.5 mass %, it is extremely difficult to form a glass, and when a molten glass is cooled during mass production there is the problem that the glass might be colored. In addition, it might be difficult for antimicrobial properties to be exhibited after a hot water or hydrothermal treatment.

Examples of the alkaline earth metal oxide in the vitreous antimicrobial agent of the present invention include MgO, CaO, SrO, and BaO, and CaO and BaO are preferable when the ease of forming a glass and the resistance to coloration of the glass itself are taken into consideration. The percentage content of the alkaline earth metal oxide in the vitreous antimicrobial agent is 2 to 10 mass %, preferably 3 to 8 mass %, and more preferably 4 to 7.5 mass %. If the vitreous antimicrobial agent contains more than 10 mass % of the alkaline earth metal oxide, since the relative proportion of the antimicrobial component ZnO, etc., is decreased, it might become difficult for the antimicrobial effect to be exhibited, and since the proportions of the glass framework-forming components $B_2O_3$ and $SiO_2$ decrease, it might become difficult to form a glass. On the other hand, if the alkaline earth metal oxide is less than 2 mass %, it might also become difficult to form a glass.

The percentage content of $Na_2O$ in the vitreous antimicrobial agent of the present invention is 6 to 7.5 mass %. If the vitreous antimicrobial agent contains more than 7.5 mass % of $Na_2O$, since the relative proportion of the antimicrobial component ZnO, etc., is decreased, it might become difficult for the antimicrobial effect to be exhibited, and since the proportions of the glass framework-forming components $B_2O_3$ and $SiO_2$ decrease, it might become difficult to form a glass. On the other hand, if the $Na_2O$ is less than 6 mass %, the antimicrobial effect might not be exhibited sufficiently.

The percentage content of $CeO_2$ in the vitreous antimicrobial agent of the present invention is preferably 0.01 to 5 mass %, and more preferably 0.01 to 2 mass %. If the vitreous antimicrobial agent contains more than 5 mass % of $CeO_2$, since the relative proportions of other essential vitreous antimicrobial agent components decrease, it might become difficult for the antimicrobial effect to be exhibited, and since the proportions of glass framework-forming components decrease, it might become difficult to form a glass. On the other hand, if no $CeO_2$ is contained, the glass itself might be easily colored.

Since the vitreous antimicrobial agent of the present invention contains little glass framework-forming components, it might be difficult to form a glass. Furthermore, since $Ag_2O$, which is easily reduced, is added, there is a tendency for coloration or for it to be difficult to form a glass. Hence, by adding a specified oxidizing agent to a starting material formulation of the vitreous antimicrobial agent it is possible to prepare a vitreous antimicrobial agent in which $Ag_2O$ is resistant to reduction, coloration is prevented, and the antimicrobial activity is stabilized.

Preferred components of the oxidizing agent include nitrates such as ammonium nitrate, sodium nitrate, zinc nitrate, silver nitrate, barium nitrate, calcium nitrate, and magnesium nitrate, antimony oxide, and an arsenic compound, and the nitrates are most preferable from the viewpoint of safety and absence of the influence of residues in the glass. The percentage content of the oxidizing agent in the vitreous antimicrobial agent is at most 20 mass % relative to the glass component. When zinc nitrate or silver nitrate is used as the oxidizing agent, it is added while taking into consideration the concentrations of ZnO and $AgO_2$ in the vitreous antimicrobial agent.

Essential glass components in the present invention include $Ag_2O$, ZnO, $SiO_2$, $B_2O_3$, an alkaline earth metal oxide, and $Na_2O$, and as long as each of the above-mentioned glass components is in the corresponding compositional range of the present invention, another glass-forming component may be added as required. However, $Al_2O_3$ and $P_2O_5$ are undesirable components since they are highly likely to degrade the hot water resistance of the vitreous antimicrobial agent of the present invention. Preferred examples include $ZrO_2$ and $TiO_2$; and if desired $Li_2O$ and $K_2O$ and a so-called 'modifying component', for example, a fluorine compound such as sodium fluoride or aluminum fluoride, can be added as appropriate. They are effective in accelerating melting of the glass and improving moldability, but if a large amount of glass-forming component and/or modifying component is added to the vitreous antimicrobial agent, there is a possibility that the hot water resistance of the glass might be degraded or the characteristics of the present invention might be impaired, and the content is therefore preferably at most 2 mass % relative to the glass components, and more preferably at most 1 mass %.

When the vitreous antimicrobial agent of the present invention is added to a resin, the agent is usually used in the form of a powder, and it is generally preferable for the average particle size to be equal to or less than 30 μm from the viewpoint of dispersion in the resin; in particular, when the agent is processed into a product such as a fiber, a paint, or a film, it is preferable to employ an agent having an average particle size of equal to or less than 15 μm and a maximum particle size of equal to or less than 20 μm so as not to degrade the physical properties of the product. The finer the particle size of the vitreous antimicrobial agent of the present invention, the easier it is for discoloration of the resin and for process failures such as secondary aggregation to occur, and the average particle size is therefore preferably between 3 μm and 15 μm. In the vitreous antimicrobial agent of the present invention, when the grain size is adjusted by grinding glass lumps obtained by melting and cooling, there is a possibility of contamination with coarse material, and it is therefore preferable to remove the coarse material by passing through a sieve after grinding, etc.

The average particle size referred to in the present invention is an average particle size on a volume basis measured by a laser diffraction method.

When producing the vitreous antimicrobial agent of the present invention, a known production process can be employed. In general, a glass starting material formulation or a mixture of this starting material formulation and an oxidizing agent is melted in a melting furnace at 900° C. to 1700° C., the melt is rapidly cooled, and the lump glass thus obtained is ground to give a desired glass powder.

In order for excellent antimicrobial properties to be exhibited compared with conventional products, the antimicrobial agent of the present invention has a high content of ZnO, and has lower concentrations of $SiO_2$ and $B_2O_3$, which are glass framework-forming components, compared with conventional vitreous antimicrobial agents, and it might be difficult to form a glass, particularly during mass production on a commercial basis. Taking this into consideration, a glass is obtained easily by melting at an appropriate melting temperature and employing rapid cooling means suitable for the cooling characteristics of the melt. When the cooling speed is slow, part of the starting material components might precipitate, thus causing coloration, or they might not become a glass in parts, thus forming a nonuniform composition.

In order to enhance the cooling effect, increasing the contact area between the melt and a cooling body is effective; for example, an extremely high cooling effect can be achieved by passing the molten glass at high speed through metal rollers cooled by means of a cooling medium such as water, and in accordance with this cooling method it is easy to form a glass. When cooling is carried out by this method, since the glass coming out between the rollers is molded into a thin sheet, it is extremely easy to grind it into a powder.

When the antimicrobial agent of the present invention is kneaded into a resin, the antimicrobial performance is exhibited by the antimicrobial agent that is present on the surface of a resin molding, and when the resin molding is subjected to rubbing, cleaning, or washing, this antimicrobial agent might come off from the surface of the resin molding. When the extent to which it comes off is high, the antimicrobial effect deteriorates and the effect might disappear in a very short period of time.

When the antimicrobial agent of the present invention is kneaded into a resin, etc., by enhancing contact or adhesion between the antimicrobial agent and the resin, it is possible to improve the dispersibility of the antimicrobial agent and to prevent the antimicrobial agent from coming off from the surface of the resin composition. In this case, it is also possible to treat the surface of the vitreous antimicrobial agent powder with a surface treatment agent such as a silane coupling agent or a silicone oil.

With regard to the surface treatment agent used in the present invention, the most suitable one may be selected appropriately according to the intended application, the type of resin, the processing method, etc., and any treatment agent may be used as long as it is conventionally used for the surface treatment of an inorganic powder, and is not particularly limited.

Specific examples of the surface treatment agent include vinylsilanes such as vinyltriethoxysilane and vinyltrimethoxysilane; (meth)acryloxysilanes and glycidoxysilanes such as γ-methacryloxypropyltrimethoxysilane and γ-glycidoxypropyltrimethoxysilane; coupling agents such as tetraethoxysilane, titanium tetraisopropoxide, and aluminum ethylate; and silicone oils such as dimethyl silicone, methylphenyl silicone, methyl hydrogen silicone, reactive silicone, and non-reactive silicone.

The surface treatment method is not particularly limited, and any method that is conventionally known as a surface treatment method for an inorganic powder may be used. Examples thereof include a dry method, a wet method, a spray method, and a gasification method. As an efficient surface treatment method, there is a method in which, when grinding a glass into a powder, a mixture of lump glass and the surface treatment agent is ground in a grinder. Use of this method allows the surface treatment to be carried out at the same time.

The antimicrobial agent of the present invention may be used singly, but when it is used in combination with another antimicrobial agent, the antimicrobial properties can be further enhanced so as to suit various types of processing and required performance.

With regard to an antimicrobial agent used in combination with the antimicrobial agent of the present invention, an inorganic compound having silver and/or zinc supported thereon or an organic antimicrobial agent can be used. Examples of an inorganic compound on which silver and/or zinc are to be supported are as follows. That is, there are inorganic absorbents such as activated alumina and silica gel, and inorganic ion exchangers such as zeolite, calcium phosphate, zirconium phosphate, titanium phosphate, potassium titanate, hydrated bismuth oxide, hydrated zirconium oxide, and hydrotalcite. Furthermore, the antimicrobial effect can be further improved by adding zinc oxide or a vitreous antimicrobial agent that has a different glass composition from that of the vitreous antimicrobial agent of the present invention and that has a different particle size, solubility, etc.

It is also possible to improve rapid-acting properties or antimold effect by adding an organic antimicrobial agent or an antimold agent. The organic antimicrobial agent is not particularly limited, and examples thereof are as follows. That is, there are quaternary ammonium salt-based compounds, glycerol fatty acid esters (e.g. fatty acid monoglycerides), biguanide-based compounds, bronopol, phenol-based compounds, anilide-based compounds, iodine-based compounds, imidazole-based compounds, thiazole-based compounds, isothiazolone-based compounds, triazine-based compounds, nitrile-based compounds, chitosan, tropolone-based compounds, and organometallic-based compounds (zinc pyrithione, OBPA).

In order to improve the kneading processability with a resin and other physical properties, various types of additives may be added to the antimicrobial agent of the present invention as necessary. Specific examples thereof include a pigment such as zinc oxide or titanium oxide, an inorganic ion exchanger such as zirconium phosphate or zeolite, a dye, an antioxidant, a light stabilizer, a flame retardant, an antistatic agent, a foaming agent, an impact modifier, a glass fiber, a lubricant such as a metal soap, a desiccant, a filler, a coupling agent, a nucleating agent, a flowability improving agent, a deodorant, wood flour, an antimold agent, an antifoulant, a corrosion inhibitor, a metal powder, a UV absorber, and a UV shielding agent.

An antimicrobial resin composition can easily be obtained by adding the antimicrobial agent of the present invention to a resin. The type of resin that can be used is not particularly limited; the resin may be any of a natural resin, a synthetic resin, and a semi-synthetic resin, and the resin may be either a thermoplastic resin or a thermosetting resin. The resin may be any one of a molding resin, a fiber resin, and a rubber resin, and specific examples of the resin include molding or fiber resins such as polyethylene, polypropylene, vinyl chloride, ABS resin, AS resin, MBS resin, nylon resin, polyester, polyvinylidene chloride, polystyrene, polyacetal, polycarbonate, PBT, acrylic resin, fluorine resin, polyurethane elastomer, polyester elastomer, melamine, urea resin, ethylene tetrafluoride resin, unsaturated polyester resin, rayon, acetate, acrylic, polyvinyl alcohol, cupra, triacetate, and vinylidene, and rubber resins such as natural rubber, silicone rubber, styrene butadiene rubber, ethylene propylene rubber, fluorine rubber, nitrile rubber, chlorosulfonated polyethylene rubber, butadiene rubber, synthetic natural rubber, butyl rubber, urethane rubber, and acrylic rubber. The antimicrobial agent of the present invention may be formed into a composite with a fiber such as a natural fiber, thus giving an antimicrobial fiber.

The percentage content of the antimicrobial agent of the present invention in the antimicrobial resin composition of the present invention is preferably 0.03 to 5 parts by mass relative to 100 parts by mass of the antimicrobial resin composition, and more preferably 0.1 to 2.0 parts by mass. If it is less than 0.03 parts by mass, the antimicrobial properties of the antimicrobial resin composition might be insufficient, and on the other hand if it is present at more than 5 parts by mass, there is hardly any further improvement of the antimicrobial effect, it is not cost-effective, and the physical properties of the resin might be greatly degraded.

A method for adding the antimicrobial agent of the present invention to a resin and processing into a resin molding may be any known method. For example, there are (1) a method in which an attachment agent for enhancing the adhesion between an antimicrobial agent powder and a resin or a dispersant for improving the dispersibility of the antimicrobial agent powder is used, and mixing with the resin in the form of pellets or a powder is carried out directly in a mixer, (2) a method in which mixing is carried out as described above, the mixture is molded into pellets using an extruder, and this molding is then added to resin pellets, (3) a method in which the antimicrobial agent is molded into high concentration pellets using a wax, etc., and the pellets thus molded are then added to resin pellets, and (4) a method in which a paste composition is prepared by mixing and dispersing the antimicrobial agent in a highly viscous liquid such as a polyol, and this paste is then added to resin pellets.

When molding the above-mentioned antimicrobial resin composition, any known processing techniques and equipment may be used according to the characteristics of various types of resins. Preparation can be easily carried out by a mixing, addition, or kneading method while heating at an appropriate temperature and applying an appropriate increased or decreased pressure; specific operations may be carried out by a standard method, and moldings in various forms such as lump, sponge, film, sheet, filament, pipe, or a composite thereof may be obtained.

With regard to the antimicrobial product thus obtained, since the antimicrobial agent of the present invention, which is a component of the antimicrobial product, has excellent antimicrobial properties and discoloration resistance, it does not deteriorate during mixing of the antimicrobial agent and the resin, during subsequent storage of the antimicrobial resin composition, or during application of the product.

The form in which the antimicrobial agent of the present invention is used is not particularly limited, and it is not limited to being added to a resin molding or a polymer compound. It may be mixed, according to the intended application where antimold, antialgal, and antibacterial properties are required, with another component as appropriate or may be made into a composite with another material. For example, it may be used in various forms such as a powder, a powder-containing dispersion, granules, an aerosol, or a liquid.

Application

The antimicrobial agent of the present invention can be used in various fields where antimold, antialgal, and antibacterial properties are required, that is, it can be used as an electrical appliance, a kitchen product, a fiber product, a building material product, a toiletry product, a paper product, a toy, a leather product, stationery, and other products.

To illustrate more specific applications, examples of the electric appliances include dish washers, dish dryers, refrigerators, washing machines, pots, televisions, personal computers, radio cassettes, cameras, video cameras, water purifiers, rice cookers, vegetable cutters, cash registers, bedding dryers, Faxes, ventilators, and air-conditioners, and examples of the kitchen products include tableware, chopping boards, straw cutters, trays, chopsticks, teapots, thermos bottles, knives, ladle handles, turners, lunch boxes, rice spoons, bowls, colanders, sink strainers, scouring brush containers, bins, and draining bags.

Examples of the fiber products include shower curtains, mattress fillings, air-conditioner filters, stockings, socks, napkins, sheets, bedding covers, pillows, gloves, aprons, curtains, diapers, bandages, masks, and sportswear, and examples of the building materials include decorative boards, wall paper, flooring boards, window films, handles, carpets, mats, artificial marble, handrails, jointing, tiles, and waxes. Examples of the toiletry products include toilet seats, bathtubs, tiles, potties, bins, toilet brushes, bathtub covers, pumice stones, soap containers, bathroom chairs, linen baskets, showers, and basins, examples of the paper products include wrapping paper, powder paper, medicine boxes, sketch books, patient charts, notebooks, and origami paper, and examples of the toys include dolls, soft toys, papier-mache, blocks, and puzzles.

Examples of the leather products include shoes, bags, belts, watch straps, interior products, chairs, gloves, and hanging straps, and examples of the stationery include ball-point pens, mechanical pencils, pencils, rubbers, crayons, paper, diaries, floppy disks, rulers, labels (e.g., Post-it), and staplers.

Examples of the other products include insoles, cosmetics containers, scouring brushes, powder puffs, hearing aids, musical instruments, cigarette filters, adhesive paper sheets for cleaning, hanging strap handles, sponges, kitchen towels, cards, microphones, hairdressing equipment, vending machines, razors, telephones, medical thermometers, stethoscopes, slippers, clothing cases, toothbrushes, sandpit sand, food wrapping films, antimicrobial sprays, and paint.

Effect

The vitreous antimicrobial agent of the present invention comprising a high concentration of ZnO and an appropriate amount of $Ag_2O$ has a high antimicrobial effect, and is useful as an antimicrobial agent that can be used with various types of resins. ZnO exhibits an effect in a wide variety of resins and easily exhibits an effect on *Staphylococcus aureus*, and $Ag_2O$ tends to particularly easily exhibit an effect with an olefin resin with regard to the type of resin and on *E. coli* with regard to the type of microbe. It is surmised that the antimicrobial agent comprising these two microbial components at high concentrations exhibits a high antimicrobial effect. However, when commercial production of on the order of at least a few hundred kg is carried out, there are restrictions on the contents of zinc and silver and the amount of other glass-forming components added, and the glass might be colored when a specific mixture ratio is not used. On the other hand, if $SiO_2$ and $B_2O_3$, which are necessary as glass framework-forming components in order to form uniform glass, are added in large amounts, there is a tendency for the exhibition of a high antimicrobial effect to be inhibited. As a result of an intensive investigation, a vitreous antimicrobial agent having a high antimicrobial effect can be obtained by minimizing the percentage contents of $SiO_2$ and $B_2O_3$ and adding appropriate amounts of an alkaline earth metal oxide and $Na_2O$. Since an appropriate amount of $Ag_2O$, which is difficult to make into a glass and is easily reduced, is added to a glass starting material mixture, by adding $CeO_2$ thereto the vitreous antimicrobial agent can be obtained stably.

INDUSTRIAL APPLICABILITY

By strictly controlling the composition of the glass component, the silver- and zinc-containing vitreous antimicrobial agent of the present invention can be produced at a commercial scale without coloration. The antimicrobial agent of the present invention has a high antimicrobial effect, can maintain the antimicrobial effect in various types of resins for a long period of time, and has coloration resistance, and is therefore very useful as an antimicrobial agent for use in a wide range of applications.

Furthermore, by adding the antimicrobial agent of the present invention to a resin, an antimicrobial resin composition that exhibits excellent long-lasting performance with respect to antimicrobial properties, discoloration resistance, and hot water resistance can easily be obtained. Moreover, an antimicrobial product comprising the antimicrobial agent of the present invention has excellent antimicrobial properties, discoloration resistance, and durability.

EXAMPLES

The present invention is explained in further detail below by reference to Examples, but the present invention should not be construed as being limited thereby. The values in Table 1 are mass %.

Example 1

Preparation of Vitreous Antimicrobial Agent 600 kg of a glass starting material formulation having the composition of Example 1 shown in Table 1 was heated and melted at 1100° C. to 1300° C. After melting, cooling was carried out, and the glass thus obtained was dry-ground using a ball mill to give a vitreous antimicrobial agent powder having an average particle size of about 9 μm.

Example 2

Preparation of Vitreous Antimicrobial Agent 600 kg of a glass starting material formulation having the composition of Example 2 shown in Table 1 was subjected to the same operation as in Example 1 to give a vitreous antimicrobial agent powder.

Comparative Example 1 to Comparative Example 9

For Comparative Examples 1, 2, 5, and 6, the procedure of Example 1 was repeated except that glass starting material formulations (100 kg each) having the compositions shown in Table 1 were used to give vitreous powders. For Comparative Examples 3, 4, 7, 8, and 9, the procedure of Example 1 was repeated except that glass starting material formulations having the compositions shown in Table 1 were used to give vitreous powders.

For Comparative Examples 3 and 4, the glass was partially colored pale yellow during cooling after melting, and for Comparative Examples 8 and 9, the entire glass was colored pale yellow during cooling after melting. When the colored glass was used for a white to pale color processed resin product, the color of the processed resin product was changed to yellow and therefore could not be used often in practice, but the glass was subjected to the various types of evaluation below.

TABLE 1

|  | $Ag_2O$ | ZnO | $SiO_2$ | $B_2O_3$ | $P_2O_5$ | CaO | BaO | $Na_2O$ | $CeO_2$ |
|---|---|---|---|---|---|---|---|---|---|
| Ex. 1 | 1.2 | 48.0 | 7.5 | 31.6 |  | 5.0 |  | 6.3 | 0.4 |
| Ex. 2 | 0.7 | 43.3 | 8.0 | 34.0 |  | 3.0 | 4.0 | 7.0 |  |
| Comp. Ex. 1 | 0.0 | 49.2 | 7.5 | 31.6 |  | 5.0 |  | 6.3 | 0.4 |
| Comp. Ex. 2 | 1.2 | 37.0 | 9.5 | 36.6 |  | 5.0 | 3.0 | 7.3 | 0.4 |
| Comp. Ex. 3 | 1.2 | 46.9 | 10.5 | 31.6 |  | 3.5 |  | 6.3 |  |
| Comp. Ex. 4 | 1.2 | 48.0 | 8.5 | 29.6 |  | 6.0 |  | 6.3 | 0.4 |
| Comp. Ex. 5 | 1.2 | 48.0 | 7.5 |  | 31.6 | 5.0 |  | 6.3 | 0.4 |
| Comp. Ex. 6 | 1.2 | 42.0 | 7.5 | 32.0 |  | 5.0 | 6.0 | 6.3 |  |
| Comp. Ex. 7 | 1.2 | 48.0 | 6.4 | 32.0 |  | 3.5 |  | 8.9 |  |
| Comp. Ex. 8 | 1.2 | 51.0 | 6.4 | 31.6 |  | 3.5 |  | 6.3 |  |
| Comp. Ex. 9 | 2.5 | 46.7 | 7.5 | 31.6 |  | 5.0 |  | 6.3 | 0.4 |

Example 3

Preparation of Test Molding Plate, Coloration, Antimicrobial Test, Hot Water Resistance Test 0.5 mass % of the vitreous antimicrobial agents obtained in Examples 1 and 2 and Comparative Examples 1 to 9 were added to a polypropylene resin (Grand Polypro J707Z, manufactured by Grand Polymer Co., Ltd.), and the mixtures were injection-molded at a molding temperature of 240° C. using an M-50AII-DM injection molder manufactured by Meiki Co., Ltd. to give 11 cm×11 cm×2 mm evaluation molding plates (Nos. 1 to 11).

For comparison, the polypropylene resin alone was injection-molded in the same manner without adding any glass to give a comparative molding plate (No. X).

Furthermore, the antimicrobial activity (initial antimicrobial effect and antimicrobial effect after immersion in hot water) of the molding plates was evaluated in accordance with JIS Z2801. The detailed procedure of the method for evaluating the antimicrobial activity was as follows.

Various types of resin molding plates were cut into dimensions of 5 cm×5 cm, and the surface thereof was wiped with ethanol to give evaluation samples. As test microbes, E. coli and Staphylococcus aureus were used, and an inoculation test microbial suspension was prepared by diluting a nutrient broth medium to 1/500 using purified water to give a solution having a viable cell count of 2.5 to $10 \times 10^5$/mL. 0.4 mL of the inoculation test microbial suspension was dropped on the surface of a sample, it was covered with a 4.0 cm×4.0 cm polyethylene film so as to make uniform contact with the surface, and it was stored at a temperature of 35° C. and a humidity of 95 RH % for 24 hours. The viable cell count was measured by a standard agar pour-plate method (37° C., 2 days) using a washing obtained by washing surviving cells from the top of the sample with 10 mL of cell count measurement medium (SCDLP liquid medium) 0 hours (cell count immediately after inoculation) and 24 hours after starting storage, and converting into a viable cell count per sheet of sample. The results of the evaluation of the antimicrobial effects thus obtained are expressed as the difference between the logarithm of the viable cell count of each molding plate and the logarithm of the viable cell count of the comparative molding plate No. X for each resin, and are given in Table 2. The higher the value of the difference, the higher the antimicrobial effect. The cell counts immediately after inoculation were $2.0 \times 10^5$ per plate for E. coli and $3.7 \times 10^5$ for Staphylococcus aureus, the viable cell counts for comparative molding plate No. X were $1.5 \times 10^7$ and $2.7 \times 10^5$ for E. coli and Staphylococcus aureus respectively, and the viable cell counts for comparative molding plate No. Y, which was Plate No. X after immersing it in ion-exchanged water at 50° C. for 16 hours, were $1.3 \times 10^7$ and $2.6 \times 10^5$ for E. coli and Staphylococcus aureus respectively.

Hot Water Immersion (Hot Water Resistance Test), Antimicrobial Effect, and Color Each molding plate was immersed in ion-exchanged water at 50° C. for 16 hours. The molding plate after hot water immersion was used as a sample, and the antimicrobial activity was evaluated in the same manner as above. The results are given in Table 2. It is possible to evaluate the hot water resistance of the antimicrobial effect by the degree to which the antimicrobial effect after hot water immersion decreased compared with the initial effect. The color of each molding plate after the hot water resistance test was examined visually.

TABLE 2

| | | Antimicrobial activity evaluation | | | | |
|---|---|---|---|---|---|---|
| | | Initial antimicrobial effect (difference in viable cell count) | | Antimicrobial effect after hot water immersion (difference in viable cell count) | | Color of molding plate after hot water |
| Molding Plate No. | Type of vitreous antimicrobial agent | E. coli | Staphylococcus aureus | E. coli | Staphylococcus aureus | resistance test |
| 1 | Ex. 1 | 6.2< | 4.4< | 6.1< | 4.4< | Colorless |
| 2 | Ex. 2 | 6.2< | 4.4< | 6.1< | 4.4< | Colorless |
| 3 | Comp. | 4.1 | 3.4 | 0.4 | 0.7 | Colorless |

TABLE 2-continued

| | | Antimicrobial activity evaluation | | | | |
|---|---|---|---|---|---|---|
| | | Initial antimicrobial effect (difference in viable cell count) | | Antimicrobial effect after hot water immersion (difference in viable cell count) | | Color of molding plate after hot water |
| Molding Plate No. | Type of vitreous antimicrobial agent | E. coli | Staphylococcus aureus | E. coli | Staphylococcus aureus | resistance test |
| 4 | Ex. 1 Comp. Ex. 2 | 5.8 | 2.1 | 2.0 | 0.3 | Colorless |
| 5 | Comp. Ex. 3 | 6.2< | 3.7 | 1.6 | 1.9 | Pale yellow |
| 6 | Comp. Ex. 4 | 5.8 | 1.9 | 2.4 | 1.1 | Pale yellow |
| 7 | Comp. Ex. 5 | 6.2< | 4.4< | 4.9 | 2.8 | Dark yellow |
| 8 | Comp. Ex. 6 | 6.2< | 3.8 | 1.9 | 0.5 | Pale yellow |
| 9 | Comp. Ex. 7 | 6.2< | 4.2 | 0.9 | 0.8 | Pale yellow |
| 10 | Comp. Ex. 8 | 6.2< | 4.4< | 2.9 | 3.8 | Yellow |
| 11 | Comp. Ex. 9 | 6.2< | 4.4< | 6.1< | 4.4< | Yellow |

The molding plates (No. 1 and 2) to which antimicrobial agents formed from the glasses of Examples 1 and 2 of the present invention were added had excellent antimicrobial properties and excellent coloration resistance.

Compared with the antimicrobial agent of the present invention, the molding plate (No. 3) to which was added the antimicrobial agent formed from the glass of Comparative Example 1, which contained no $Ag_2O$, had a rather poor antimicrobial effect, and the effect after the hot water resistance test was particularly degraded.

The molding plate (No. 4) to which was added the antimicrobial agent formed from the glass of Comparative Example 2, which had a rather low ZnO content and contained large amounts of $SiO_2$ and $B_2O_3$, also had a rather poor antimicrobial effect, and the initial antimicrobial effect and the effect after the hot water resistance test, in particular toward *Staphylococcus aureus*, were degraded.

Compared with the antimicrobial agent of the present invention, the molding plate (No. 5) to which was added the antimicrobial agent formed from the glass of Comparative Example 3, which contained a large amount of $SiO_2$, had an initial effect, but the antimicrobial effect after the hot water resistance test deteriorated greatly. The color of the molding plate after the hot water resistance test was slightly yellowish.

Compared with the antimicrobial agent of the present invention, the molding plate (No. 6) to which was added the antimicrobial agent formed from the glass of Comparative Example 4, which contained a slightly smaller amount of $B_2O_3$, had a rather poor antimicrobial effect, and the antimicrobial effect after the hot water resistance test deteriorated particularly greatly. The color of the molding plate after the hot water resistance test was slightly yellowish.

Compared with the antimicrobial agent of the present invention, the molding plate (No. 7) to which was added the antimicrobial agent formed from the glass of Comparative Example 5, which contained $P_2O_5$ and did not contain $B_2O_3$, had an adequate antimicrobial effect, but the molding plate became yellow after the hot water resistance test.

Compared with the antimicrobial agent of the present invention, the molding plates (Nos. 8 and 9) to which were added the antimicrobial agents formed from the glasses of Comparative Examples 6 and 7, which contained a larger amount of an alkaline earth metal oxide or $Na_2O$, had an initial antimicrobial effect, but the antimicrobial effect deteriorated after the hot water resistance test, and the color of the molding plates was slightly yellowish.

Compared with the antimicrobial agent of the present invention, the glass of Comparative Example 8 and the glass of Comparative Example 9, which contained a larger amount of ZnO or $Ag_2O$ respectively, were colored, and the molding plates (Nos. 10 and 11) to which these antimicrobial agents were added had an adequate antimicrobial effect, but the color of the molding plates was yellow.

The invention claimed is:

1. A vitreous antimicrobial agent comprising, relative to 100 mass % of total glass components, 0.1 to 2 mass % of $Ag_2O$, 40.5 to 49 mass % of ZnO, 6 to 9.5 mass % of $SiO_2$, 30.5 to 39.5 mass % of $B_2O_3$, 2 to 10 mass % of an alkaline earth metal oxide, and 6 to 7.5 mass % of $Na_2O$.

2. The vitreous antimicrobial agent according to claim 1, wherein the glass components further comprise 0.01 to 5 mass % of $CeO_2$.

3. The vitreous antimicrobial agent according to claim 1, wherein the vitreous antimicrobial agent is a powder and has an average particle size of 0.1 to 30 μm.

4. An antimicrobial resin composition comprising the vitreous antimicrobial agent according to claim 1 in an amount at which an antimicrobial function is exhibited.

5. An antimicrobial resin composition comprising the vitreous antimicrobial agent according to claim 2 in an amount at which an antimicrobial function is exhibited.

6. An antimicrobial resin composition comprising the vitreous antimicrobial agent according to claim 3 in an amount at which an antimicrobial function is exhibited.

7. An antimicrobial resin composition comprising the vitreous antimicrobial agent according to claim 1 at 0.03 to 5 parts by mass relative to 100 parts by mass of the antimicrobial resin composition.

8. An antimicrobial resin composition comprising the vitreous antimicrobial agent according to claim 2 at 0.03 to 5 parts by mass relative to 100 parts by mass of the antimicrobial resin composition.

9. An antimicrobial resin composition comprising the vitreous antimicrobial agent according to claim 3 at 0.03 to 5 parts by mass relative to 100 parts by mass of the antimicrobial resin composition.

10. An antimicrobial product comprising the vitreous antimicrobial agent according to claim 1.

11. An antimicrobial product comprising the vitreous antimicrobial agent according to claim 2.

12. An antimicrobial product comprising the vitreous antimicrobial agent according to claim 3.

* * * * *